(12) United States Patent
Bozano et al.

(10) Patent No.: US 8,530,136 B2
(45) Date of Patent: Sep. 10, 2013

(54) FLUOROALCOHOL CONTAINING MOLECULAR PHOTORESIST MATERIALS AND PROCESSES OF USE

(75) Inventors: Luisa D. Bozano, Los Gatos, CA (US); Gregory Breyta, San Jose, CA (US); Ekmini A. DeSilva, Ossining, NY (US); William D. Hinsberg, Fremont, CA (US); Ratnam Sooriyakumaran, San Jose, CA (US); Linda K. Sundberg, Los Gatos, CA (US)

(73) Assignee: International Business Machines Corporation, Armonk, NY (US)

( * ) Notice: Subject to any disclaimer, the term of this patent is extended or adjusted under 35 U.S.C. 154(b) by 182 days.

(21) Appl. No.: 12/971,292

(22) Filed: Dec. 17, 2010

(65) Prior Publication Data

US 2012/0156611 A1    Jun. 21, 2012

(51) Int. Cl.
| G03F 7/004 | (2006.01) |
| G03F 7/20  | (2006.01) |
| G03F 7/30  | (2006.01) |
| G03F 7/38  | (2006.01) |

(52) U.S. Cl.
USPC ........ 430/270.1; 430/311; 430/325; 430/326; 430/330; 430/907; 558/268; 568/720

(58) Field of Classification Search
None
See application file for complete search history.

(56) References Cited

U.S. PATENT DOCUMENTS

| 5,679,495 A | 10/1997 | Yamachika et al. |
| 6,093,517 A | 7/2000 | Ito et al. |
| 6,197,473 B1 | 3/2001 | Kihara et al. |
| 6,713,225 B2 | 3/2004 | Iida et al. |
| 2008/0026317 A1 | 1/2008 | Breyta et al. |
| 2009/0042123 A1 | 2/2009 | Kinoshita et al. |
| 2010/0047709 A1 | 2/2010 | Echigo et al. |

FOREIGN PATENT DOCUMENTS

| CA | 1204547 | 11/1982 |
| JP | 1293339 A | 11/1989 |
| WO | WO2009143357 | 11/2009 |

OTHER PUBLICATIONS

Chang, Seung Wook, et al., "Sub-50 nm feature sizes using positive tone molecular glass resists for EUV lithography", (c) The Royal Society of Chemistry 2006, J. Mater. Chem, 2006, vol. 16, pp. 1470-1474.
Ito, Hiroshi et al., "Characterization and Lithographic Application of Calix[4]resorcinarene Derivatives", Chem. Mater. 2008, vol. 20, pp. 341-356, published on web Dec. 11, 2007; (c) 2008 American Chemical Society.
English Abstract for JP1293339(A) furnished by espacenet—Bibliographic data, at http://v3.espacenet.com/publicationDetails/biblio?CC-JP&NR-1293339A&KC-A&FT=. . ., downloaded Nov. 18, 2010; 1 page.
Okuyama, Kenichi "Molecular resists based on calix[4]resorcinarene derivatives for EB lithography" Advances in Resist Materials and Processing Technology, XXVI, Proc. of SPIE vol. 7273, (c) 2009 SPIE, pp. 72732U-1 through 72732U-7.
Reichmanis, E. et al., "Chemical Amplification Mechanisms for Microlithography", Reviews; (c) 1991 American Chemical Society; Chem. Mater. 1991, vol. 3, No. 3, (1991) pp. 394-407.
Shiono, Daiju et al. "Distribution control of protecting groups and its effect on LER for EUV molecular resist", Advances in Resist Materials and Processing Technology XXIV, (2007) Proc. of SPIE, vol. 7519, pp. 65193U-1 through 65193U-6.
Bjerre et al; "Synthesis of Some Trifluoromethylated Cyclodextrin Derivatives and Analysis of Their Properties as Artificial Glycosidases and Oxidases," Eur. J. Org. Chem 2007, 704-710.
De Silva et al; "Hexafluoroalcohol (HFA) containing molecular resist materials for high resolution lithographic applications," Proc. of Spie, vol. 7972, 79721Z-10, (2011).
International Search Report and Written Opinion issued in International Application No. PCT/EP2011/070579 dated Feb. 22, 2012; 11 pages.
Matshushita Denki Sangyo KK; "Database WPI week 200661; Thomsom Scientific, Lindon GB; AN 2006-589091 XP002667905 and JP2006208765A," 4 pages, Aug. 10, 2006 (abstract).

*Primary Examiner* — Sin J. Lee
(74) *Attorney, Agent, or Firm* — Cantor Colburn LLP

(57) ABSTRACT

Phenolic molecular glasses such as calixarenes include at least one fluoroalcohol containing unit. The fluoroalcohol containing molecular glasses can be used in photoresist compositions. Also disclosed are processes for generating a resist image on a substrate using the photoresist composition.

13 Claims, 6 Drawing Sheets

FLUOROALCOHOL CONTAINING MOLECULAR PHOTORESIST MATERIALS AND PROCESSES OF USE

BACKGROUND

The present invention relates to molecular glass photoresists containing fluoroalcohol functionalities.

As the minimum critical dimension continues to shrink to less than 50 nanometers (nm), it is becoming increasingly difficult to simultaneously meet critical performance criteria, sensitivity, resolution, and line edge roughness (LER). The size of polymers typically employed in chemical amplification photoresists is beginning to influence performance at these dimensions. For example, it is believed that the magnitude of line edge roughness is directly correlated to the molecular weight of the base polymer in the photoresist. As a result, a number of photoresists based on low molecular weight polymers or non-polymers have been proposed to address the performance issues needed for these advanced design rules.

Molecular glass resists have gained attention as a potential candidate for next generation resist materials. Such small molecules termed "molecular glasses" (MGs) possess structural features that inhibit crystallization and display relatively high glass transition temperatures (Tg) despite their modest size. MGs combine characteristic properties of small molecules such as high purity and well defined structure with beneficial aspects of polymers such as high thermal stability and thin film forming properties. The small molecular size of 1 to 2 nanometers (nm) is expected to facilitate high-resolution patterning due to the possibility of reducing the "pixel" size of the basic imaging unit.

This new class of resist materials has shown progress in terms of resolution, sensitivity and LER. However, although MGs offer potential advantages over polymeric resists in terms of molecular size, there are many challenges with the synthesis and processing of these materials. One of the main issues with these materials is the poor solubility in a casting solvent that prevents the formation of good quality thin films. Another challenge is the ability to synthesize monodisperse materials. In previously published systems, a molecular glass resist consisted of a matrix with a core structure that is functionalized with an average number of acid labile protecting groups. These resist materials have a distribution of protecting groups. Chromatography based purification methods were used to obtain monodisperse units which showed superior performance compared to the disperse matrix. In order to obtain a monodisperse material that showed improved performance required very tedious synthetic and purification processes. Another issue is that several MG systems require diluted developer due to their high dissolution rates and therefore incompatible with 0.26N tetramethylammonium hydroxide (TMAH), the conventional developer.

Therefore to advance this resist platform, there is a need to develop molecular glass materials that are monodisperse, readily soluble in casting solvents, compatible with 0.26N TMAH developer, and easy to synthesize.

SUMMARY

Disclosed herein is a phenolic molecular glass having at least one fluoroalcohol containing unit, a photoresist composition including the phenolic molecular glass having at least one fluoroalcohol containing unit and a photoacid generator, and a process for generating a resist image on a substrate. The phenolic molecular glass can be a calixarene such as a calix[4]resorcinarene of structural formula (I):

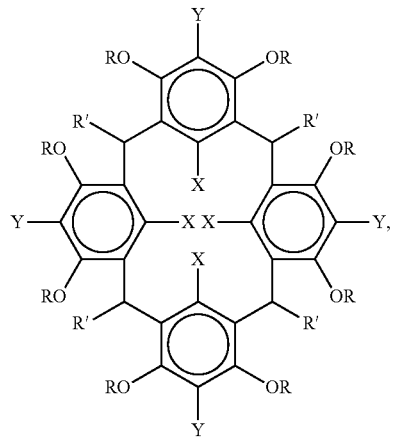

wherein R' comprises the at least one fluoroalcohol containing unit and R is independently selected from the group consisting of hydrogen and an acid labile functional group.

The X and Y moieties may be the same or different and are selected from the group consisting of hydrogen, alkyl, alkenyl, alkynyl, alkoxy, aryl, aralkyl, alkaryl, halo, cyano, nitro and carboxylate.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter, which is regarded as the invention, is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Figure 1:
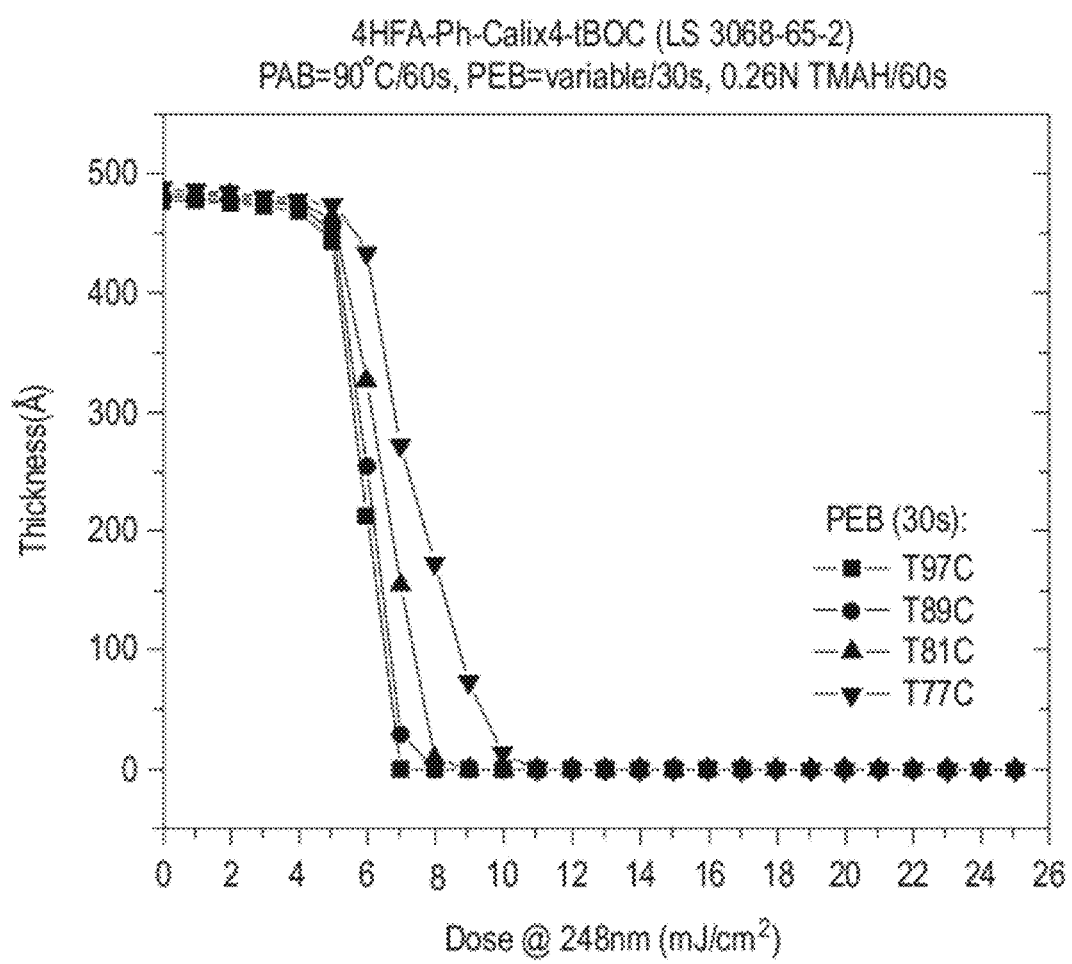
FIG. 1 graphically illustrates contrast curves at 248 nm as a function of post exposure bake (PEB) temperature in 0.26 N TMAH developer for a hexafluoroalcohol containing molecular glass resist in accordance with the present invention.

The present invention relates to fluoroalcohol containing molecular glass resist materials for high resolution lithographic applications. The fluoroalcohol containing molecular glass resist materials are monodisperse; readily soluble in casting solvents; compatible with 0.26N TMAH developer; and easy to synthesize.

In describing and claiming the present invention, the following terminology will be used in accordance with the definitions set out below.

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. The term "lower alkyl" intends an alkyl group of one to six carbon atoms, preferably one to four carbon atoms, and the term "lower alkyl ester" refers to an ester functionality —C(O)O—R wherein R is a lower alkyl.

The term "alkenyl" as used herein refers to a branched or unbranched hydrocarbon group of 2 to 24 carbon atoms containing at least one double bond, typically containing one to six double bonds, more typically one or two double bonds, e.g., ethenyl, n-propenyl, n-butenyl, octenyl, decenyl, and the like, as well as cycloalkenyl groups such as cyclopentenyl, cyclohexenyl and the like. The term "lower alkenyl" intends an alkenyl group of two to six carbon atoms, preferably two to four carbon atoms.

The term "alkynyl" as used herein refers to a branched or unbranched hydrocarbon group of 2 to 24 carbon atoms containing at least one triple bond, e.g., ethynyl, n-propynyl, n-butynyl, octynyl, decynyl, and the like, as well as cycloalkynyl groups such as and the like. The term "lower alkynyl" intends an alkynyl group of two to six carbon atoms, preferably two to four carbon atoms.

The term "alkoxy" as used herein refers to a substituent—O—R wherein R is alkyl as defined above. The term "lower alkoxy" refers to such a group wherein R is lower alkyl.

The term "aryl" as used herein, and unless otherwise specified, refers to an aromatic moiety containing one to five aromatic rings. For aryl groups containing more than one aromatic ring, the rings may be fused or linked. Preferred monocyclic aromatic substituents are phenyl and substituted phenyl, optionally substituted with one to five, typically one to four, halo, alkyl, alkenyl, alkynyl, alkoxy, nitro or other substituents.

The term "halo" is used in its conventional sense to refer to a chloro, bromo, fluoro or iodo substituent. The terms "haloalkyl," "haloaryl" (or "halogenated alkyl" or "halogenated aryl") refers to an alkyl or aryl group, respectively, in which at least one of the hydrogen atoms in the group has been replaced with a halogen atom.

The term "alkaryl" refers to an aryl group with an alkyl substituent, wherein "aryl" and "alkyl" are as defined above.

The term "aralkyl" refers to an alkyl group that has an aryl substituent, wherein "alkyl" and "aryl" are as defined above.

The term "fluorinated" refers to replacement of a hydrogen atom in a molecule or molecular segment with a fluorine atom, and includes perfluorinated moieties. The term "perfluorinated" is also used in its conventional sense to refer to a molecule or molecular segment wherein all hydrogen atoms are replaced with fluorine atoms. Thus, a "fluorinated" methyl group encompasses —CH$_2$F and CHF$_2$ as well as the "perfluorinated" methyl group, i.e., —CF$_3$ (trifluoromethyl). The term "fluoroalkyl" refers to a fluorinated alkyl group, the term "fluoroalkylene" refers to a fluorinated alkylene linkage, the term "fluoroalicyclic" refers to a fluorinated alicyclic moiety, and the like.

The terms "photogenerated acid" and "photoacid" are used interchangeably herein to refer to the acid that is created upon exposure of the present compositions to radiation, i.e., as a result of the radiation-sensitive acid generator in the compositions.

The terms "acid-labile" or "acid-cleavable" are used interchangeably herein to refer to a molecular moiety that undergoes a change in structure upon contact with a strong acid, e.g., a carboxylic ester that, upon contact with a sulfonic acid is converted to a carboxylic acid, a carbonate ester that, upon contact with acid is converted to a hydroxyl group, or the like. The groups that are "acid-labile" or "acid-cleavable" in the context of the present invention are also referred to as "acid-labile functionalities".

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

For additional information concerning terms used in the field of lithography and lithographic compositions, reference may be had to Introduction to Microlithography, 2$^{nd}$ Edition, Eds. L. Thompson et al. (Washington, D.C.: American Chemical Society, 1994).

In one embodiment, the fluoroalcohol containing molecular glass resist materials are calixarenes. By way of example, the calixarenes can be fluoroalcohol containing calix[4]resorcinarenes having the structure of formula (I) below.

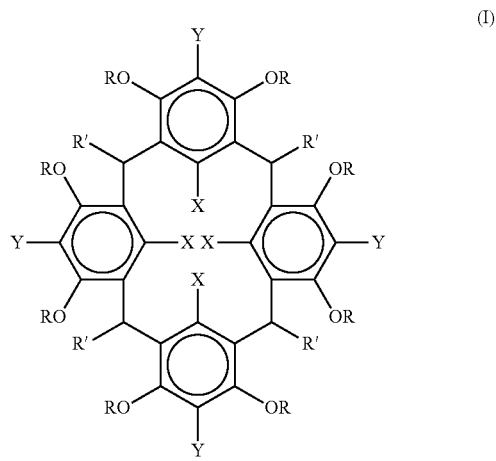

(I)

In one embodiment, at least one of the R' moieties contain a fluoroalcohol functionality and the R moieties represent hydrogen and/or acid-labile functional groups. The various fluoroalcohol containing calix[4]resorcinarenes are condensation products of resorcinols and fluoroalcohol containing aldehydes. It will be appreciated that the symmetric location of the —OR moieties in the calix[4]resorcinarene of formula (I) corresponds to the positioning of the —OR moieties on the resorcinol starting material used to make these compounds.

The R' moieties including the fluoroalcohol functionality are of the general formula (II):

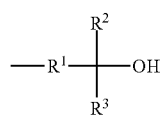

(II)

wherein $R^1$ is a linear or branched alkylene group, a substituted or unsubstituted alicyclic group, a substituted or unsubstituted arylene group, a substituted or unsubstituted heteroarylene group, a substituted or unsubstituted heterocyclic group;

$R^2$ and are $R^3$ are each independently fluorinated alkyl group, wherein the fluorinated alkyl group may be the same or different.

Suitable acid-labile functional groups include, but are not limited to, moieties having the structure of formula (III)

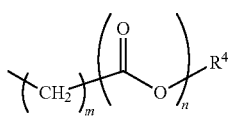

(III)

in which m is 0 to 4, n is 0 or 1, and $R^4$ is $CR^5R^6R^7$, or $SiR^8R^9R^{10}$, wherein $R^5$, $R^6$ and $R^7$ are independently hydrogen, alkyl, alkoxy, aryl, or aryloxy, typically hydrogen, lower alkyl or lower alkoxy, or are linked to form a cycloalkyl or cyclooxyalkyl ring, typically a five- to twelve-membered ring, and $R^8$, $R^9$ and $R^{10}$ are the same or different and are each an alkyl, typically a lower alkyl, substituent.

Thus, $R^4$ may be, for example, methoxymethyl, ethoxymethyl, methoxyethoxymethyl, benzyloxymethyl, cyclopropylmethyl, diphenylmethyl, triphenylmethyl, 1-methoxyethyl, 1,1-dimethoxyethyl, 1-ethoxyethyl, 1-ethylthio ethyl, 1,1-diethoxyethyl, 1-phenoxyethyl, 1,1-diphenoxyethyl, 1-cyclopropylethyl, 1-phenylethyl, 1,1-diphenylethyl, t-butyl, 1,1-dimethylpropyl, 1-methylbutyl, 1,1-dimethylbutyl, methylcyclopentyl, ethylcyclopentyl, methylcyclohexyl, ethylcyclohexyl, methylcyclooctyl, ethylcyclooctyl, methyladamantyl, ethyladamantyl, trimethylsilyl, ethyldimethylsilyl, diethylmethylsilyl, triethylsilyl, dimethylisopropylsilyl, t-butyldimethylsilyl, di-t-butylmethylsilyl, tri-t-butylsilyl, dimethylphenylsilyl, methyldiphenylsilyl, triphenylsilyl, trimethylgermyl, ethyldimethylgermyl, diethylmethylgermyl, triethylgermyl, dimethylisopropylgermyl, methyldiisopropylgermyl, triisopropylgermyl, t-butyldimethylgermyl, di-t-butylmethylgermyl, tri-t-butylgermyl, dimethylphenylgermyl, methyldiphenylgermyl, triphenylgermyl, and the like. Other suitable acid-labile protecting groups may be found in the pertinent literature and texts (e.g., Greene et al., Protective Groups in Organic Synthesis, $2^{nd}$ Ed., John Wiley & Sons, 1991).

Representative —OR moieties are illustrated in formulas (IV)-(IX) below.

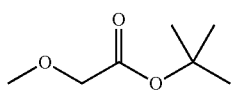

(IV)

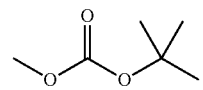

(V)

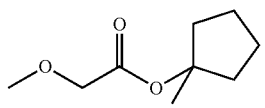

(VI)

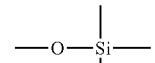

(VII)

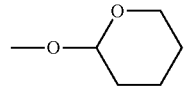

(VIII)

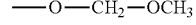

(IX)

The X and Y moieties may be the same or different and are selected from the group consisting of hydrogen, alkyl, alkenyl, alkynyl, alkoxy, aryl, aralkyl, alkaryl, halo, cyano, nitro and carboxylate. In certain embodiments, the X moieties are all hydrogen, and the Y moieties are selected from the group consisting of hydrogen and lower alkyl.

The basic calix[4]resorcinarene molecule can exist in either of two isomeric forms, commonly referred to as the $C_{2V}$ and the $C_{4V}$ configurations (also sometimes referred to herein as the "ctt" and "ccc" isomers, respectively). These isomers can be separated by fractional crystallization using conventional techniques. In the context of the invention, the calix[4] resorcinarenes may be in either the $C_{2V}$ or the $C_{4V}$ configurations so as to provide structural monomodality. Alternatively, a mixture of isomers can be used in the blend.

The calix[4]resorcinarenes can generally be prepared by condensation reaction with resorcinol and a fluorocontaining aldehyde using hydrochloric acid as a catalyst in accordance with the following scheme.

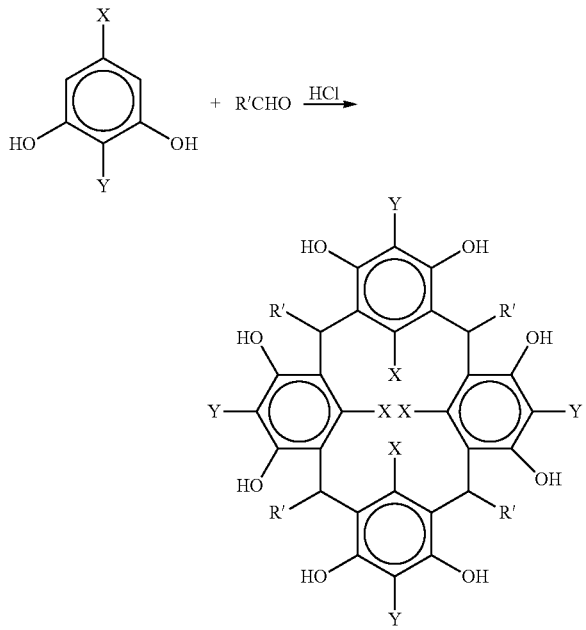

The acid labile moieties can then be introduced into the calix[4]resorcinarene molecule by reacting with the unprotected calix[4]resorcinarene with a desired moiety that will then provide an acid-labile functionality on the eight hydroxyl groups. The reaction may be conducted using conventional means known to those skilled in the art. For example, to provide a calix[4]resorcinarene with the t-butoxycarbonylmethyl (t-BuOOCCH$_2$) groups, the calix[4]esorcinarene may be reacted with eight equivalents or a slight excess of t-butyl bromoacetate and potassium carbonate. Similarly, to provide a calix[4]resorcinarene fully protected with the t-butoxycarbonyl (tBuOOC) group, the calix[4]resorcinarene may be reacted with eight equivalents or a slight excess of di-t-butyl dicarbonate. Various reaction schemes to fabricate the calix[4]resorcinarenes are known in the art and are not intended to be limited to that shown above. By way of example, the calix[4]resorcinarenes can be prepared in accordance with Ito et al., Characterization and Lithographic Application of Calix[4]resorcinarene Derivatives, Chem. Mater. 20: 341-356 (2008).

For positive tone applications, the photoresist compositions herein include fluoroalcohol containing calix[4]resorcinarenes, a photoacid generator, and a solvent. For negative tone applications, the photoresist may further include a crosslinker.

Upon exposure to radiation, the photoacid generator generates an acid that is used to cleave the acid labile groups as in the case of a positive tone resist or effect a crosslinking reaction as in the case of a negative tone resist. A variety of photoacid generators (also referred to herein as "PAGs") can be used in the composition of the present invention. Generally, suitable acid generators have a high thermal stability (preferably to temperatures greater than 140° C.) so they are not degraded during pre-exposure processing. Any suitable photoacid generator can be used in the photoresist compositions of the invention. Typical photoacid generators include, without limitation: sulfonium salts, such as triphenylsulfonium perfluoromethanesulfonate (triphenylsulfonium triflate), triphenylsulfonium perfluorobutanesulfonate, triphenylsulfonium perfluoropentanesulfonate, triphenylsulfonium perfluorooctanesulfonate, triphenylsulfonium hexafluoroantimonate, triphenylsulfonium hexafluoroarsenate, triphenylsulfonium hexafluorophosphate, triphenylsulfonium bromide, triphenylsulfonium chloride, triphenylsulfonium iodide, 2,4,6-trimethylphenyldiphenylsulfonium perfluorobutanesulfonate, 2,4,6-trimethyl-phenyldiphenylsulfonium benzenesulfonate, tris(t-butylphenyl)sulfonium perfluorooctanesulfonate, diphenylethylsulfonium chloride, and phenacyldimethylsulfonium chloride; halonium salts, particularly iodonium salts, including diphenyliodonium perfluoromethanesulfonate (diphenyl)odonium triflate), diphenyliodonium perfluorobutanesulfonate, diphenyliodonium perfluoropentanesulfonate, diphenyliodonium perfluorooctanesulfonate, diphenyliodonium hexafluoroantimonate, diphenyliodonium hexafluoroarsenate, diphenyliodonium bis-(t-butylphenyl)iodonium triflate, and bis-(di-t-butylphenyl)-iodonium camphanylsulfonate; α,α'-bissulfonyl-diazomethanes such as bis(p-toluenesulfonyl) diazomethane, methylsulfonyl p-toluenesulfonyldiazomethane, 1-cyclohexylsulfonyl-1-(1, 1-dimethylethylsulfonyl)diazomethane, and bis(cyclohexylsulfonyl)diazomethane; trifluoromethanesulfonate esters of imides and hydroxyimides, e.g., α-(trifluoromethylsulfonyloxy)-bicyclo [2.2.1]hept-5-ene-2,3-dicarboximide (MDT); nitrobenzyl sulfonate esters such as 2-nitrobenzyl p-toluenesulfonate, 2,6-dinitrobenzyl p-toluenesulfonate, and 2,4-dinitrobenzyl p-trifluoromethylbenzenesulfonate; sulfonyloxynaphthalimides such as N-camphorsulfonyloxynaphthalimide and N-pentafluorophenylsulfonyloxyna-phthalimide; pyrogallol derivatives (e.g., trimesylate of pyrogallol); naphthoquinone-4-diazides; alkyl disulfones; s-triazine derivatives, as described in U.S. Pat. No. 4,189,323; and miscellaneous sulfonic acid generators including t-butylphenyl-α-(p-toluenesulfonyloxy)-acetate, t-butyl-α-(p-toluenesulfonyloxy)acetate, and N-hydroxy-naphthalimide dodecanesulfonate (DDSN), and benzoin tosylate.

Other suitable photoacid generators are disclosed in Reichmanis et al. (1991), *Chemistry of Materials* 3:395, and in U.S. Pat. No. 5,679,495 to Yamachika et al. Additional suitable acid generators useful in conjunction with the compositions and methods provided herein will be known to those skilled in the art and/or are described in the pertinent literature.

The photoresist composition herein preferably comprises approximately 0.5-10 wt. % of the photoacid generator, and up to about 94.5 wt. % of the fluoroalcohol containing calix [4]resorcinarenes. If crosslinking agents are present, they will typically be present in the range of about 1 wt. % to 40 wt. %, preferably about 5 wt. % to 30 wt. %, of the total solids.

The crosslinking agent used in the photoresist compositions of the invention may be any suitable crosslinking agent known in the negative photoresist art, which is otherwise compatible with the other selected components of the photoresist composition. The crosslinking agents preferably act to crosslink the polymer component in the presence of a generated acid. Preferred crosslinking agents are glycoluril compounds such as tetramethoxymethyl glycoluril, methylpropyltetramethoxymethyl glycoluril, and methylphenyltetramethoxymethyl glycoluril, available under the POWDERLINK trademark from American Cyanamid Company. Other suitable crosslinking agents can also be found in Japanese Laid-Open Patent Application (Kokai) No. 1-293339, as well as etherified amino resins (for example, methylated or butylated melamine resins (N-methoxymethyl- or N-butoxymethyl-melamine, respectively)), or methylated/butylated glycolurils (for example as can be found in Canadian Patent No. 1 204 547). Combinations of crosslinking agents may be used.

Other customary additives may also be present in the photoresist composition, including pigments, sensitizers, preservatives, acid-diffusion controlling agents, coating aids such as surfactants or anti-foaming agents, adhesion promoters, plasticizers, and dissolution inhibitors, surface modifying agents, among others. Typically, the sum of all customary additives will comprise less than 20 percent of the solids included in the resist formulation, preferably, less than 5 percent.

Pigments may be used to adjust the optical density of the formulated resist and sensitizer, which can enhance the activity of photoacid generators by absorbing radiation and transferring it to the photoacid generator. Examples include aromatics such as functionalized benzenes, pyridines, pyrimidines, biphenylenes, indenes, naphthalenes, coumarins, anthraquinones, and other aromatic ketones.

A wide variety of compounds with varying basicity may be used as preservatives and acid-diffusion controlling additives. They may include nitrogenous compounds such as aliphatic primary, secondary, and tertiary amines, cyclic amines such as piperidines, pyrimidines, morpholines, aromatic heterocycles such as pyridines, pyrimidines, purines, imines such as diazabicycloundecene (DBU), guanidines, imides, amides, and others. Ammonium salts of basic anions may also be used, including ammonium, primary, secondary, tertiary, and quaternary alkyl- and arylammonium salts of alkoxides including hydroxide, phenolates, carboxylates, aryl and alkyl sulfonates, sulfonamides, and others. Other cationic nitrogenous compounds including pyridinium salts and salts of other heterocyclic nitrogenous compounds with anions such as alkoxides including hydroxide, phenolates, carboxylates, aryl and alkyl sulfonates, sulfonamides, and the like may also be employed. Surfactants may be used to improve coating uniformity, and include a wide variety of ionic and non-ionic, monomeric, oligomeric, and polymeric species. Likewise, a wide variety of anti-foaming agents may be employed to suppress coating defects. Adhesion promoters may be used as well; again, a wide variety of compounds may be employed to serve this function. A wide variety of monomeric, oligomeric, and polymeric plasticizers such as oligo- and polyethyleneglycol ethers, cycloaliphatic esters, and non-acid reactive steroidally derived materials may be used as plasticizers, if desired. However, neither the classes of compounds nor the specific compounds mentioned above are intended to be comprehensive and/or limiting. One versed in the art will recognize the wide spectrum of commercially available products that may be used to carry out the types of functions that these customary additives perform.

The remainder of the photoresist composition is composed of a solvent. The choice of solvent is governed by many factors not limited to the solubility and miscibility of resist components, the coating process, and safety and environmental regulations. Additionally, inertness to other resist components is desirable. It is also desirable that the solvent possess the appropriate volatility to allow uniform coating of films yet also allow significant reduction or complete removal of residual solvent during the post-application bake process. See, e.g., Introduction to Microlithography, Eds. Thompson et al., cited previously. Solvents may generally be chosen from ether-, ester-, hydroxyl-, and ketone-containing compounds, or mixtures of these compounds. Examples of appropriate solvents include cyclopentanone, cyclohexanone, lactate esters such as ethyl lactate, alkylene glycol alkyl ether esters such as propylene glycol methyl ether acetate, alkylene glycol monoalkyl esters such as methyl cellosolve, butyl acetate, 2-ethoxyethanol, and ethyl 3-ethoxypropionate. Preferred solvents include ethyl lactate, propylene glycol methyl ether acetate, and mixtures of ethyl lactate and ethyl 3-ethoxyproprionate. The above list of solvents is for illustrative purposes only and should not be viewed as being comprehensive nor should the choice of solvent be viewed as limiting the invention in any way. Those skilled in the art will recognize that any number of solvents or solvent mixtures may be used.

Greater than 50% of the total mass of the resist formulation is typically composed of the solvent, preferably greater than 80%.

The present invention also relates to a process for generating a resist image on a substrate comprising the steps of: (a) coating a substrate with a film comprising the resist composition of the invention; (b) imagewise exposing the film to radiation; and (c) developing the image. The first step involves coating the substrate with a film comprising the resist composition dissolved in a suitable solvent. Suitable substrates are silicon-containing, and include, for example, silicon dioxide, silicon nitride, silicon oxynitride, and chrome-coated quartz or glass. The substrate may or may not be coated with an organic anti-reflective layer prior to deposition of the resist composition. Preferably, the surface of the substrate is cleaned by standard procedures before the film is deposited thereon. Suitable solvents for the composition are as described in the preceding section, and include, for example, cyclohexanone, ethyl lactate, and propylene glycol methyl ether acetate. The film can be coated on the substrate using art-known techniques such as spin or spray coating, or doctor blading. Preferably, before the film has been exposed to radiation, the film is heated to a temperature of about 25-150° C. for a short period of time, typically on the order of about 1 minute. The dried film has a thickness of about 20-5000 nm, preferably about 50-1200 nm.

In the second step of the process, the film is imagewise exposed to activating energy such as may be provided by x-ray, electron beam (e-beam), ultraviolet radiation or extreme ultraviolet (EUV) radiation (13.4 nm). The radiation is absorbed by the radiation-sensitive photoacid generator to generate free acid, which, in the case of a positive tone resist, with heating causes cleavage of the acid-cleavable ester substituent and formation of the corresponding acid, or as in the case of a negative tone resist crosslinking. Preferably, after the film has been exposed to radiation, the film is again heated to a temperature of about 25-150° C. for a short period of time, on the order of about 1 minute.

The third step involves development of the image with a suitable solvent. Suitable solvents include an aqueous base, preferably an aqueous base without metal ions such as the industry standard developer tetramethyl ammonium hydroxide or choline. The resist composition of the invention has high radiation sensitivity and provides images exhibiting high contrast and straight walls. The composition can also be readily developed in industry standard developer. Development is without unacceptable thinning or swelling. The resist has suitable thermal properties ($T_g$), good adhesion, and planarization. In addition, the presence of the fluoroaclohol functionalities significantly improved the solubility characteristics of the composition of the present invention.

The composition of the present invention may be used to make an integrated circuit assembly, such as an integrated circuit chip, multichip module, circuit board, quartz mask, or imprint template. The integrated circuit assembly comprises a circuit formed on a substrate by the steps of (a) coating a substrate with a film comprising the resist composition of the present invention, (b) imagewise exposing the film to radiation to form a latent image therein, (c) developing the image to expose the substrate, and (d) forming the circuit in the developed film on the substrate by art-known techniques. After the substrate has been exposed, circuit patterns can be formed in the exposed areas by coating the substrate with a conductive material such as conductive metals by art-known dry techniques such as evaporation, sputtering, plating, chemical vapor deposition, or laser-induced deposition. The surface of the film can be milled to remove any excess conductive material. Dielectric materials may also be deposited by similar means during the process of making circuits. Inorganic ions such as boron, phosphorous, or arsenic can be implanted in the substrate in the process for making p-doped or n-doped circuit transistors. Other means for forming circuits are well known to those skilled in the art. The composition of the present invention may also be used to fabricate photomasks, imprint templates and the like.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

EXAMPLES

Example 1

In this example, 4-(1,1,1,3,3,3-hexafluoro-2-hydroxy-2-propyl)phenylcalix[4]resorcinarene (Structure 1 as shown below) was synthesized through an acid catalyzed condensation reaction between a hexafluoroalcohol containing aldehyde and resorcinol.

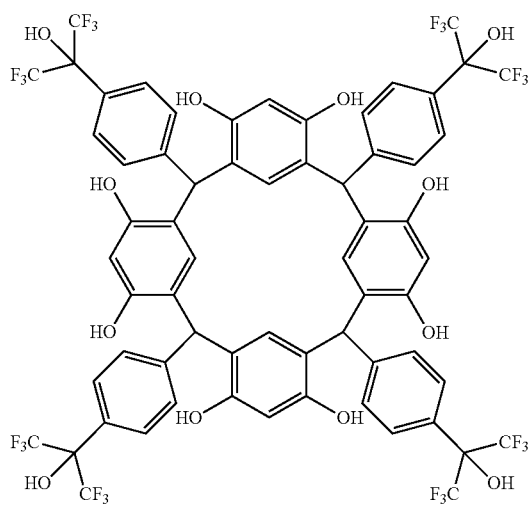

4-(1,1,1,3,3,3-hexafluoro-2-hydroxy-2-propyl)benzaldehyde (5 g, 0.018 mol), resorcinol (2 g, 0.018 mol) and methanol (20 ml) were placed in a round bottom flask equipped with a stirrer. 5 ml of concentrated hydrochloric acid was added to the mixture at room temperature and then the reaction mixture was refluxed at 70° C. for 18 hrs. The completion of the reaction was determined by the disappearance of the carbonyl peak of the aldehyde starting material through NMR or IR spectrum. The reaction solvent, methanol, was evaporated by the rotary evaporator and the resulting material was precipitated in deionized water several times. The product was confirmed by NMR spectroscopy. Yield: 4.5 g (68%). 1H-NMR (DMSO-d6): (ppm) 5.62 (s, CH, 4H), 6.16 (s, ArH, 4H), 6.21 (broad s, ArH, 2H), 6.69 (broad s, ArH, 2H), 6.81 (d, ArH, 8H), 7.39 (d, ArH, 8H), 8.38 (s, HFA-OH, 4H), 8.74 (d, Ar—OH, 8H).

xample 2

In this example, the 4-(1,1,1,3,3,3-hexafluoro-2-hydroxy-2-propyl)phenylcalix[4]resorcinarene of example 1 was selectively functionalized at the phenolic hydroxyl units with tert-butoxy carbonyl (t-BOC) groups through a base catalyzed reaction to produce t-BOC protected 4-(1,1,1,3,3,3-hexafluoro-2-hydroxy-2-propyl)phenylcalix[4]resorcinarene (structure 2 as shown below).

Structure 2

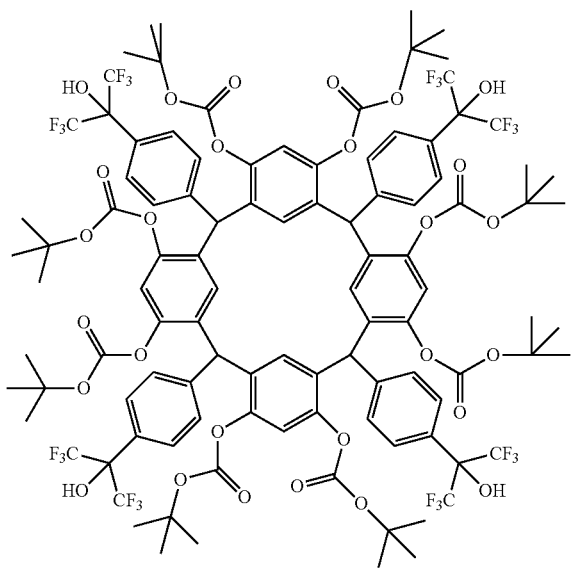

4-(1,1,1,3,3,3-hexafluoro-2-hydroxy-2-propyl)phenylcalix[4]resorcinarene (2 g, 0.0014 mol) and 4-dimethylaminopyridine (0.06 g, 0.0005 mol) were dissolved in 25 ml of acetone in a round bottom flask equipped with a stirrer. The di-tert-butyl dicarbonate (2.39 g, 0.011 mol) was added slowly using a dropping funnel and stirred at a steady pace. The evolution of $CO_2$ gas occurred immediately indicating the progress of the reaction and the reaction mixture was stirred at room temperature for 8 hrs. The solvent was reduced through evaporation and the product was purified by column chromatography with acetone as the eluent. Yellow solid was obtained. The product was confirmed by NMR spectroscopy. Yield: 2.4 g (80%). 1H-NMR (DMSO-d6): (ppm) 1.14 (s, CH3, 36H), 1.42 (s, CH3, 36H), 5.56 (s, CH, 4H), 6.33 (s, ArH, 4H), 6.78 (broad s, ArH, 8H), 7.07 (d, ArH, 2H), 7.12 (d, ArH, 2H), 7.25 (d, ArH, 8H), 8.6 (s, HFA-OH, 4H). Polydispersity: 1.02.

Example 3

In this example, a photoresist composition including the t-BOC protected 4-(1,1,1,3,3,3-hexafluoro-2-hydroxy-2-propyl)phenylcalix[4]resorcinarene of Example 2 was lithographically evaluated. The resist was formulated with 0.25 g of the t-BOC protected 4-(1,1,1,3,3,3-hexafluoro-2-hydroxy-2-propyl)phenylcalix[4]resorcinarene (Structure 2), 25 mg of triphenylsulfonium perfluoro-1-butanesulfonate (photoacid generator), and 0.75 mg of an organic base, which were dissolved in 5 g of propylene glycol monomethyl ether acetate (PGMEA). This solution was filtered through a 0.2 micron syringe filter.

The photoresist solution was spin coated onto blank silicon wafers at a thickness of about 500 angstroms using a post apply bake temperature of 90° C. for 60 seconds. FIG. 1 graphically illustrates contrast curves at 248 nm in 0.26N TMAH developer as a function of post exposure bake temperatures for 30 seconds that were generated using an ASML stepper. As shown, the resist exhibited good contrast when post exposure baked at 77° C. or higher.

Figure 2:
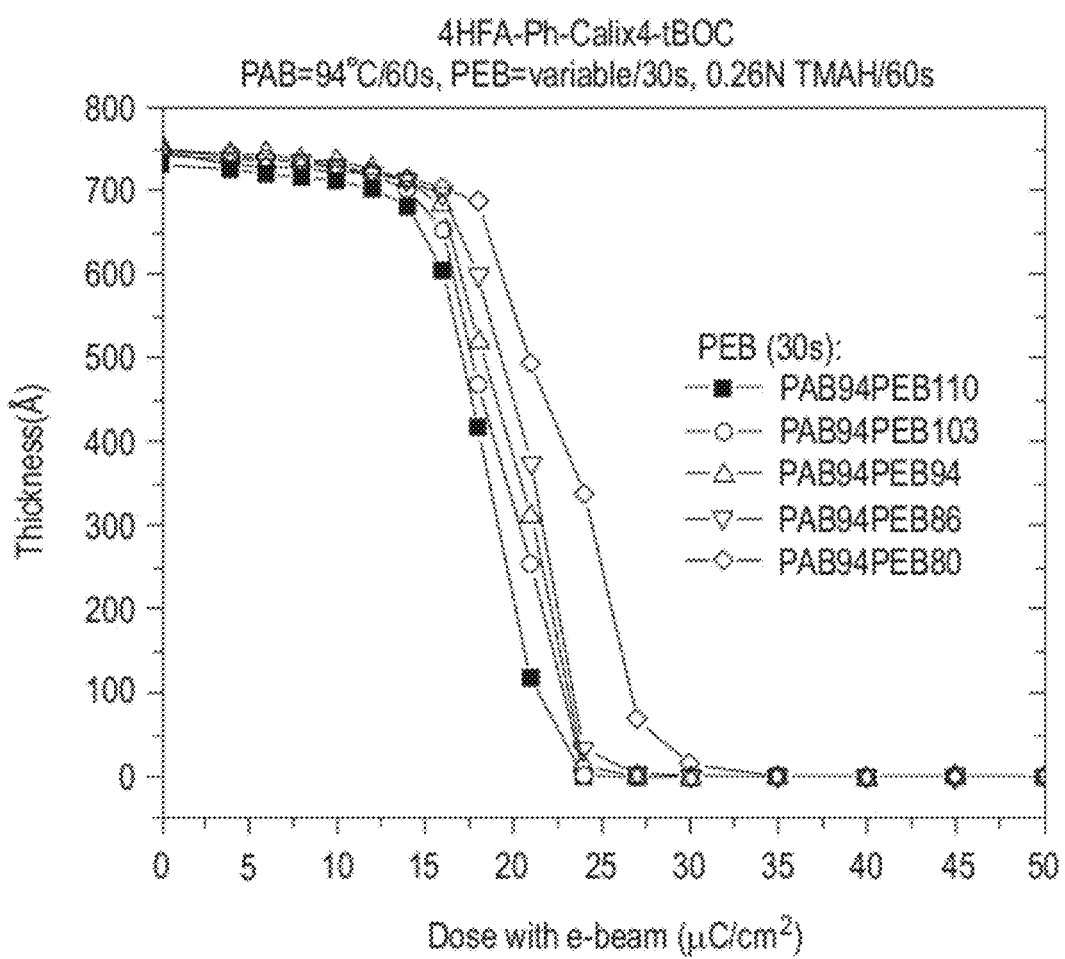
FIG. 2 graphically illustrates e-beam contrast curves as a function of post exposure bake (PEB) temperature in 0.26 N TMAH developer for a hexafluoroalcohol containing molecular glass resist in accordance with the present invention.

FIG. 2 graphically illustrates e-beam contrast curves using a 100 keV Leica e-beam exposure system in 0.26N TMAH developer as a function of post exposure bake temperature for 30 seconds. In this example, the resist was coated to a thickness of about 750 angstroms using a post apply bake temperature of 94° C. for 60 seconds.

Figure 3:
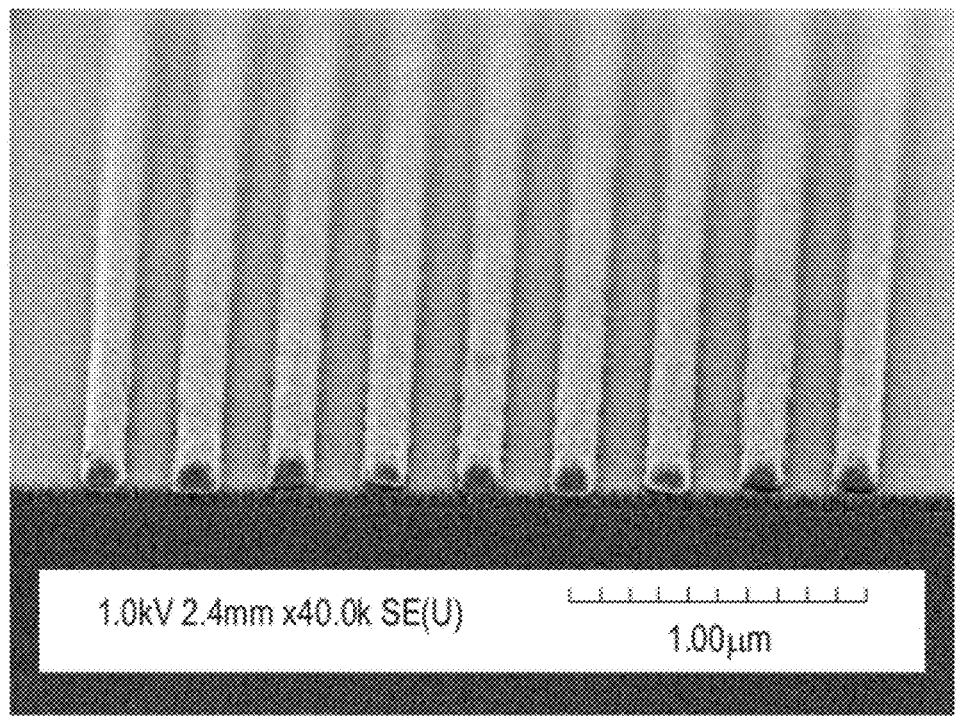
FIG. 3. pictorially illustrates scanning electron micrographs of 130 nm 1:1 line space patterns printed from a hexafluoroalcohol containing molecular glass resist in accordance with the present invention on a 0.6 NA 248 nm stepper.

Scanning electron micrographs (SEM) of 130 nm line/space patterns printed using the photoresist of example 2 on an ASML 248 nm 0.6 NA stepper are presented in FIG. 3. The exposure conditions included a post apply bake of 90° C. for 60 seconds, exposure at a dose of 14 mJ/cm², and post exposure baked at 90° C. for 30 seconds.

Figure 4:
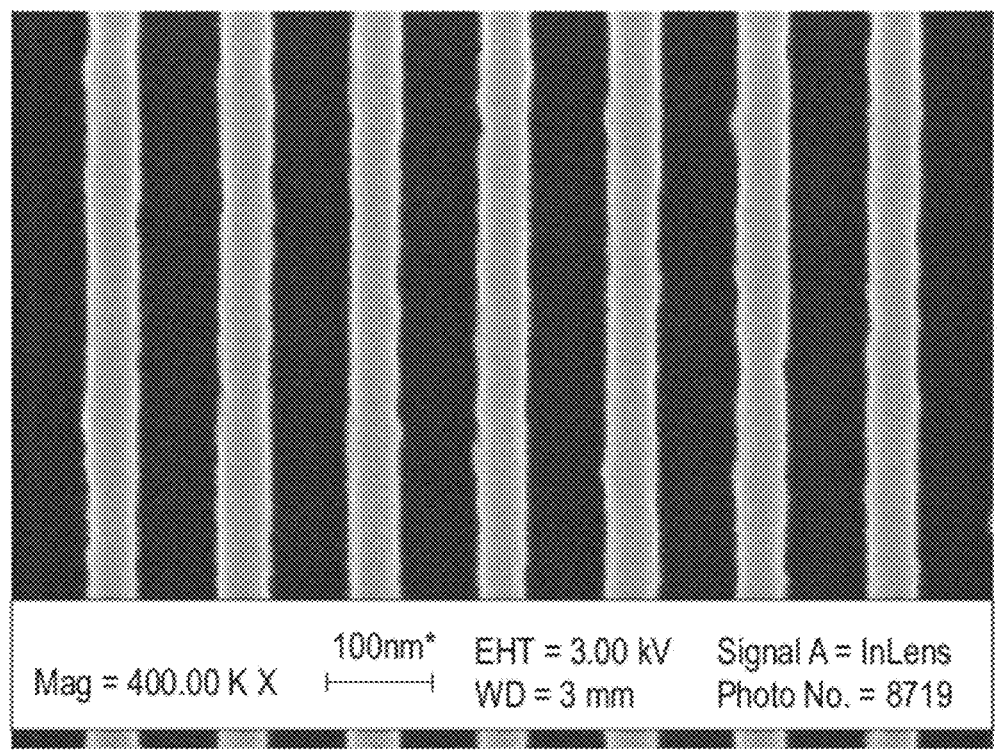
FIG. 4 pictorially illustrates scanning electron micrographs of 60 nm 1:1 line space patterns printed from a hexafluoroalcohol containing molecular glass photoresist of the present invention on a 100 KeV e-beam exposure tool.

Scanning electron micrographs (SEM) of 60 nm line/space patterns printed using the photoresist of example 2 on a 100 keV Leica e-beam exposure system are presented in FIG. 4. The exposure conditions included a post apply bake of 90° C. for 60 seconds, exposure at a dose of 75 µC/cm², and a post exposure bake at 90° C. for 30 seconds.

Figure 5:
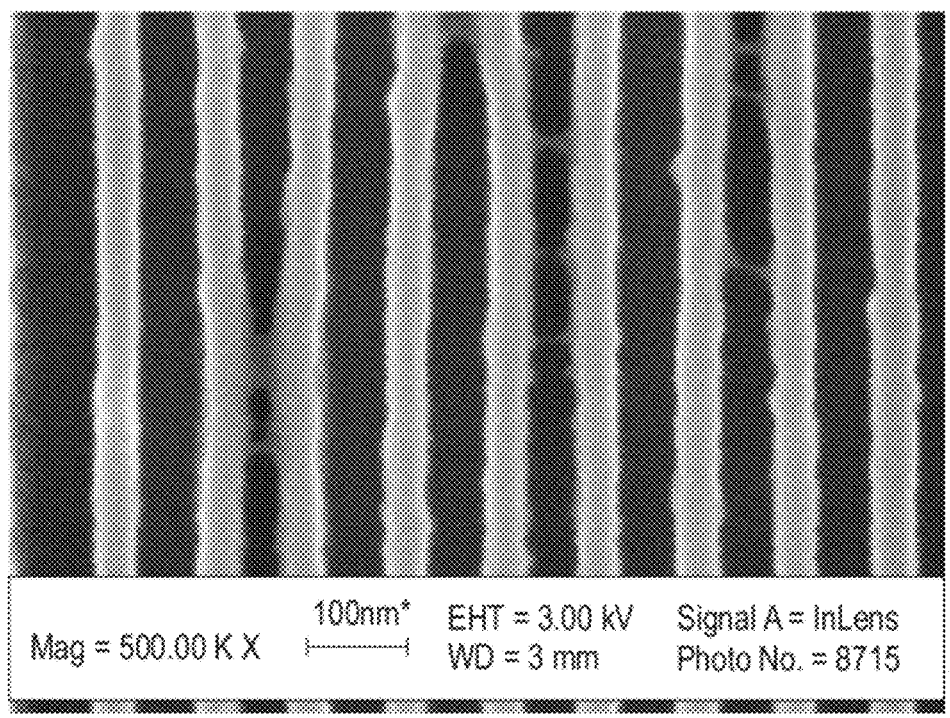
FIG. 5 pictorially illustrates scanning electron micrographs of 30/45 nm line space patterns printed from a hexafluoroalcohol containing molecular glass photoresist of the present invention on a 100 KeV e-beam exposure tool.
Figure 6:
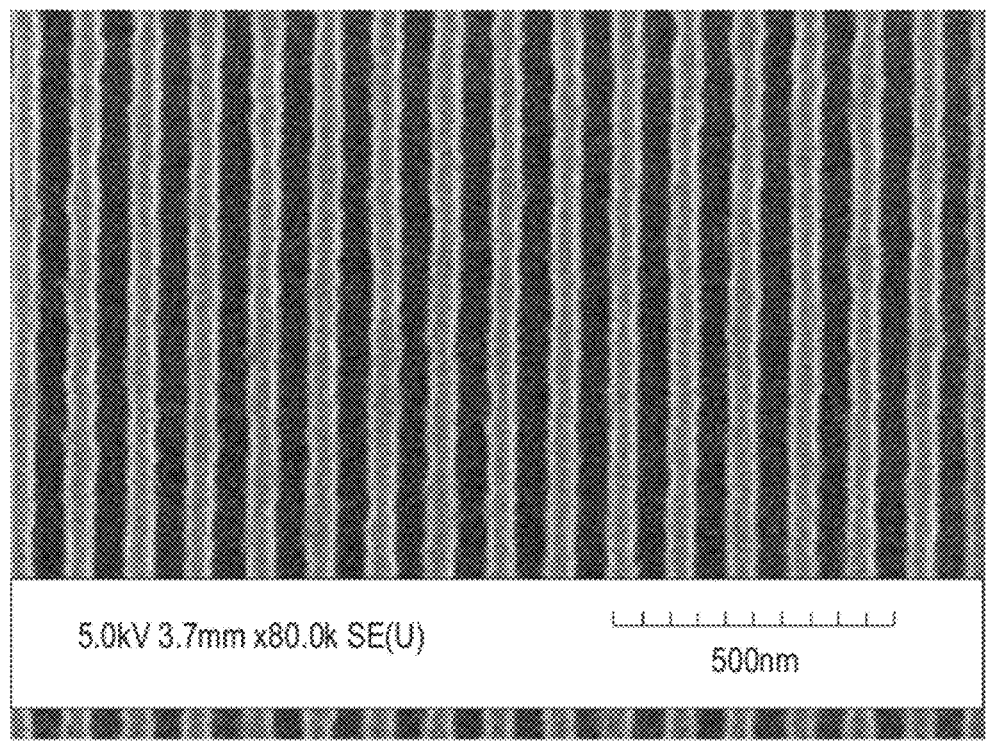
FIG. 6 pictorially illustrates scanning electron micrographs of 50 nm line space patterns printed from a hexafluoroalcohol containing molecular glass photoresist of the present invention on an extreme ultraviolet (EUV) micro exposure tool.

Scanning electron micrographs (SEM) of 30/45 nm line/space patterns printed using the photoresist of example 2 on a 100 keV Leica e-beam exposure system are presented in FIG. 5. The exposure conditions included a post apply bake of 90° C. for 60 seconds, exposure at a dose of 95 µC/cm², and a post exposure bake at 90° C. for 30 seconds.

Scanning electron micrographs (SEM) of 50 nm line/space patterns printed using the photoresist of example 2 on an EUV Micro Exposure Tool (MET) system are presented in FIG. 5. The exposure conditions included a post apply bake of 90° C.

for 60 seconds, exposure at a dose of 6 mJ/cm², and a post exposure bake at 90° C. for 30 seconds.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, and equivalents of all means or step plus function elements in the claims below are intended to include any structure, material, or for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

While the preferred embodiments to the invention have been described, it will be understood that those skilled in the art, both now and in the future, may make various improvements and enhancements which fall within the scope of the claims which follow. These claims should be construed to maintain the proper protection for the invention first described.

What is claimed is:

1. A phenolic molecular glass having at least one fluoroalcohol containing unit, wherein the phenolic molecular glass is a calix[4]resorcinarene of structural formula (I):

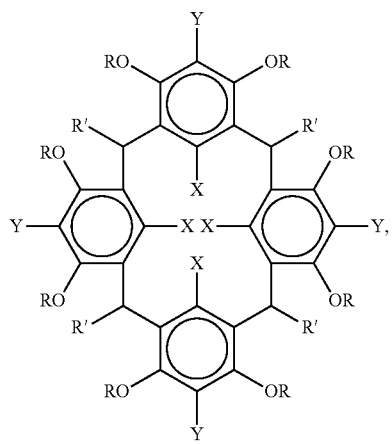

wherein R' comprises the at least one fluoroalcohol containing unit, R is independently selected from the group consisting of hydrogen and an acid labile functional group, and X and Y are each independently selected from the group consisting of hydrogen, alkyl, alkenyl, alkynyl, alkoxy, aryl, aralkyl, alkaryl, halo, cyano, nitro and carboxylate, and wherein the at least one fluoroalcohol containing unit is of the structural formula (II):

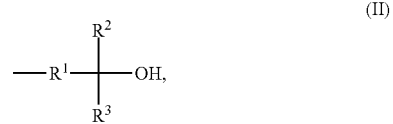

wherein R¹ is a linear or branched alkylene group, a substituted or unsubstituted alicyclic group, a substituted or unsubstituted arylene group, a substituted or unsubstituted heteroarylene group, a substituted or unsubstituted heterocyclic group; R² and are R³ are each independently a fluorinated alkyl group.

2. The phenolic molecular glass of claim 1, wherein R is an acid-labile functional group that has a structural formula (III):

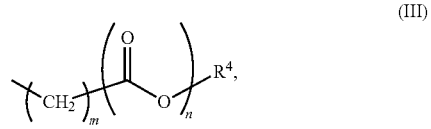

wherein m is 0 to 4, n is 0 or 1, and R⁴ is CR⁵R⁶R⁷, or SiR⁸R⁹R¹⁰, wherein R⁵, R⁶ and R⁷ are independently hydrogen, alkyl, alkoxy, aryl, or aryloxy, or are linked to form a cycloalkyl or cyclooxyalkyl ring, and R⁸, R⁹ and R¹⁰ are each an alkyl substituent.

3. The phenolic molecular glass of claim 1, wherein R is hydrogen.

4. A photoresist composition, comprising a phenolic molecular glass having at least one fluoroalcohol containing unit and a photoacid generator, wherein the phenolic molecular glass is a calix[4]resorcinarene of structural formula (I):

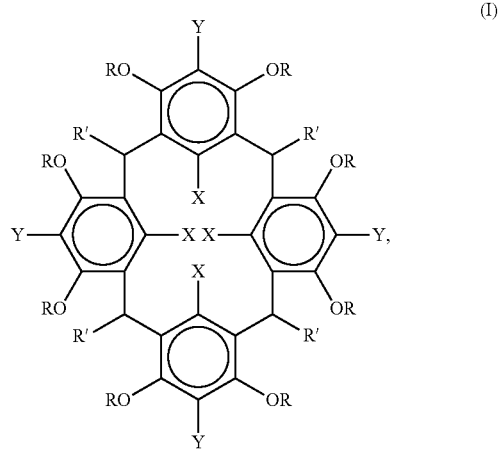

wherein R' comprises the at least one fluoroalcohol containing unit, R is independently selected from the group consisting of hydrogen and an acid labile functional group, and X and Y are each independently selected from the group consisting of hydrogen, alkyl, alkenyl, alkynyl, alkoxy, aryl, aralkyl, alkaryl, halo, cyano, nitro and carboxylate, and wherein the at least one fluoroalcohol containing unit is of the structural formula (II):

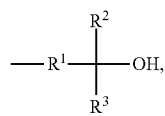

(II)

wherein $R^1$ is a linear or branched alkylene group, a substituted or unsubstituted alicyclic group, a substituted or unsubstituted arylene group, a substituted or unsubstituted heteroarylene group, a substituted or unsubstituted heterocyclic group; $R^2$ and are $R^3$ are each independently a fluorinated alkyl group.

5. The phenolic molecular glass of claim 4, wherein R is an acid-labile functional group that has a structural formula (III):

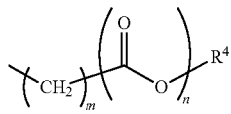

(III)

wherein m is 0 to 4, n is 0 or 1, and $R^4$ is $CR^5R^6R^7$, or $SiR^8R^9R^{10}$, wherein $R^5$, $R^6$ and $R^7$ are independently hydrogen, alkyl, alkoxy, aryl, or aryloxy, or are linked to form a cycloalkyl or cyclooxyalkyl ring, and $R^8$, $R^9$ and $R^{10}$ are each an alkyl, substituent.

6. The photoresist composition of claim 4, wherein R is hydrogen and the photoresist composition further comprises a crosslinking agent.

7. The photoresist composition of claim 4, further comprising a pigment, a sensitizer, a preservative, an acid-diffusion controlling agent, an adhesion promoter, a coating aid, a plasticizer, a surface modifying agent, and/or a dissolution inhibitor.

8. A process for generating a resist image on a substrate, comprising:
   coating a substrate with a film comprising a photoresist composition comprising a phenolic molecular glass having at least one fluoroalcohol functionality, a photoacid generator, and a solvent;
   imagewise exposing the film to radiation to form latent image therein; and
   developing the resist image with an aqueous base developer, wherein the phenolic molecular glass is a calix[4] resorcinarene of structural formula (I):

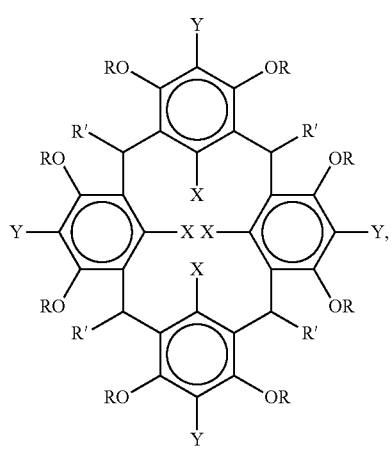

(I)

wherein R' comprises the at least one fluoroalcohol containing unit, R is independently selected from the group consisting of hydrogen and an acid labile functional group, and X and Y are each independently selected from the group consisting of hydrogen, alkyl, alkenyl, alkynyl, alkoxy, aryl, aralkyl, alkaryl, halo, cyano, nitro and carboxylate, and wherein the at least one fluoroalcohol containing unit is of the structural formula (II):

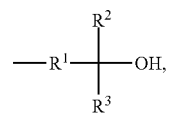

(II)

wherein $R^1$ is a linear or branched alkylene group, a substituted or unsubstituted alicyclic group, a substituted or unsubstituted arylene group, a substituted or unsubstituted heteroarylene group, a substituted or unsubstituted heterocyclic group; $R^2$ and are $R^3$ are each independently a fluorinated alkyl group.

9. The process of claim 8, wherein R is an acid labile functional group that has a structural formula (III):

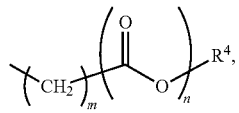

(III)

wherein m is 0 to 4, n is 0 or 1, and $R^4$ is $CR^5R^6R^7$, or $SiR^8R^9R^{10}$, wherein $R^5$, $R^6$ and $R^7$ are independently hydrogen, alkyl, alkoxy, aryl, or aryloxy, or are linked to form a cycloalkyl or cyclooxyalkyl ring, and $R^8$, $R^9$ and $R^{10}$ are each an alkyl substituent.

10. The process of claim 8, wherein R is hydrogen and the photoresist composition further comprises a crosslinker.

11. The process of claim 8, wherein subsequent to imagewise exposing the film to radiation and prior to developing, the film is heated to a temperature within a range of 25° C. to 150° C.

12. The process of claim 8, wherein the radiation is ultraviolet radiation, x-ray, EUV, or electron beam.

13. The process of claim 8, further comprising a pigment, a sensitizer, a preservative, an acid-diffusion controlling agent, an adhesion promoter, a coating aid, a plasticizer, a surface modifying agent, and/or a dissolution inhibitor.

* * * * *